(12) United States Patent
Schwab et al.

(10) Patent No.: US 12,714,368 B2
(45) Date of Patent: Aug. 25, 2026

(54) MULTI-DEVICE HEALTH PARAMETER MONITORING SYSTEMS, METHODS, AND DEVICES

(71) Applicant: GS-HealthMatrix, LLC, Los Angeles, CA (US)

(72) Inventors: Joseph Schwab, Los Angeles, CA (US); Amirhossein Yazdkhasti, Los Angeles, CA (US); Hamid Ghaednia, Los Angeles, CA (US)

(73) Assignee: GS-HEALTHMATRIX, LLC, Los Angeles, CA (US)

( * ) Notice: Subject to any disclaimer, the term of this patent is extended or adjusted under 35 U.S.C. 154(b) by 0 days.

(21) Appl. No.: 18/818,918

(22) Filed: Aug. 29, 2024

(65) Prior Publication Data

US 2025/0072791 A1 Mar. 6, 2025

Related U.S. Application Data

(60) Provisional application No. 63/579,663, filed on Aug. 30, 2023, provisional application No. 63/579,647, (Continued)

(51) Int. Cl.
*A61B 5/00* (2006.01)
*A61B 5/256* (2021.01)
(Continued)

(52) U.S. Cl.
CPC .......... *A61B 5/6831* (2013.01); *A61B 5/0093* (2013.01); *A61B 5/256* (2021.01);
(Continued)

(58) Field of Classification Search
CPC ... A61B 5/1126; A61B 5/0062; A61B 5/0077; A61B 5/4023; A61B 2562/164;
(Continued)

(56) References Cited

U.S. PATENT DOCUMENTS 5,299,454 A * 4/1994 Fuglewicz ........... A61B 5/1038 600/592
6,063,046 A * 5/2000 Allum .................... A61B 5/389 600/595
(Continued)

FOREIGN PATENT DOCUMENTS

AU 2005328364 A1 * 9/2006 ......... G06V 40/1324
CA 2928972 C * 3/2022 ........... A01K 29/005
(Continued)

OTHER PUBLICATIONS

International Search Report and Written Opinion for PCT/US2024/044434 mailed (Applicant—GS-Healthmatrix, LLC) (11 Pages).
(Continued)

*Primary Examiner* — Oommen Jacob
(74) *Attorney, Agent, or Firm* — NORTON ROSE FULBRIGHT US LLP

(57) ABSTRACT

Systems, methods, and devices include a platform with a transparent material which defines a first measurement surface. Light surfaces are positioned to provide light into the transparent material and cause a Frustrated Total Internal Reflection (FTIR) event responsive to contact at the first measurement surface. The system also includes one or more wearable devices having a base material operable to cover a portion of a human body. An inner surface of the base material defines a second measurement surface. Furthermore, one or more sensors disposed on the base material are operable to collect data at the second measurement surface. Additionally, the health parameter monitoring system presents at the display, such as a virtual reality (VR) headset, locomotion regimen information. The system collects first health parameter data from the first measurement surface based on the FTIR event; and/or second health parameter data from the second measurement surface.

20 Claims, 6 Drawing Sheets

Related U.S. Application Data filed on Aug. 30, 2023, provisional application No. 63/579,605, filed on Aug. 30, 2023, provisional application No. 63/579,616, filed on Aug. 30, 2023, provisional application No. 63/579,627, filed on Aug. 30, 2023, provisional application No. 63/579,633, filed on Aug. 30, 2023, provisional application No. 63/579,640, filed on Aug. 30, 2023.

(51) Int. Cl.

| | |
|---|---|
| ***A61B 5/296*** | (2021.01) |
| ***A61B 5/395*** | (2021.01) |
| ***A61B 7/00*** | (2006.01) |
| ***A61N 1/04*** | (2006.01) |
| ***A61N 7/00*** | (2006.01) |

(52) U.S. Cl.

CPC .............. *A61B 5/296* (2021.01); *A61B 5/395* (2021.01); *A61B 5/4523* (2013.01); *A61B 5/6803* (2013.01); *A61B 5/6806* (2013.01); *A61B 7/006* (2013.01); *A61N 1/0484* (2013.01); *A61N 7/00* (2013.01); *A61B 2560/0468* (2013.01); *A61B 2562/0204* (2013.01); *A61B 2562/046* (2013.01); *A61B 2562/066* (2013.01); *A61B 2562/164* (2013.01); *A61N 2007/0078* (2013.01)

(58) Field of Classification Search

CPC ............ A61B 17/7002; A61B 17/7062; A61B 17/06166; A61B 17/064; A61B 2017/00893; A61B 17/8625; A61B 17/80; A61B 2017/00902; A61F 2/30767; A61F 2/481; A61F 2/32; A61F 2002/30667; A61N 1/0484

See application file for complete search history.

(56) References Cited

U.S. PATENT DOCUMENTS

| | | | | |
|---|---|---|---|---|
| 6,259,108 | B1 | 7/2001 | Antonelli et al. | |
| 6,355,937 | B2 | 3/2002 | Antonelli et al. | |
| 7,849,619 | B2 | 12/2010 | Mosher, Jr. et al. | |
| 8,441,467 | B2 | 5/2013 | Han | |
| 9,501,145 | B2 | 11/2016 | Poupyrev et al. | |
| 9,524,424 | B2 * | 12/2016 | Greene | A61B 5/112 |
| 10,668,305 | B2 | 6/2020 | Cheatham, III et al. | |
| 11,238,264 | B2 | 2/2022 | Reinhold et al. | |
| 11,531,756 | B1 | 12/2022 | Raguin et al. | |
| 2005/0265585 | A1 | 12/2005 | Rowe | |
| 2007/0203435 | A1 * | 8/2007 | Novak | A43B 17/00 601/46 |
| 2008/0288200 | A1 * | 11/2008 | Noble | G01P 15/00 702/96 |
| 2009/0240170 | A1 * | 9/2009 | Rowley | A61B 5/6831 600/595 |
| 2009/0306484 | A1 | 12/2009 | Kurtz et al. | |
| 2010/0007896 | A1 | 1/2010 | Fishbaine | |
| 2012/0095283 | A1 | 4/2012 | Andersson et al. | |
| 2012/0162081 | A1 | 6/2012 | Stark | |
| 2012/0190989 | A1 | 7/2012 | Kaiser et al. | |
| 2013/0109030 | A1 | 5/2013 | Hardeman et al. | |
| 2013/0119237 | A1 | 5/2013 | Raguin et al. | |
| 2013/0253387 | A1 | 9/2013 | Bonutti et al. | |
| 2014/0121479 | A1 | 5/2014 | O'Connor et al. | |
| 2014/0303508 | A1 * | 10/2014 | Plotnik-Peleg | A61B 5/112 600/595 |
| 2015/0038812 | A1 * | 2/2015 | Ayaz | A61B 5/14553 600/328 |
| 2015/0042979 | A1 | 2/2015 | Chimmalgi et al. | |
| 2015/0351690 | A1 | 12/2015 | Toth et al. | |
| 2016/0038038 | A1 | 2/2016 | Kovacs | |
| 2017/0156662 | A1 | 6/2017 | Goodall et al. | |
| 2017/0157430 | A1 | 6/2017 | Cheatham, III et al. | |
| 2017/0319096 | A1 | 11/2017 | Kaiser et al. | |
| 2018/0018492 | A1 | 1/2018 | Vilenskii et al. | |
| 2018/0055016 | A1 * | 3/2018 | Hsieh | A01K 13/006 |
| 2018/0242860 | A1 | 8/2018 | LeBoeuf et al. | |
| 2018/0353365 | A1 | 12/2018 | Harry et al. | |
| 2019/0080158 | A1 * | 3/2019 | Roberson | G06V 40/10 |
| 2019/0105517 | A1 | 4/2019 | Tyler | |
| 2019/0290198 | A1 * | 9/2019 | Belson | A61B 5/4878 |
| 2019/0346925 | A1 | 11/2019 | Daniels | |
| 2020/0146397 | A1 | 5/2020 | Coupe et al. | |
| 2020/0276438 | A1 | 9/2020 | Bouton et al. | |
| 2021/0000590 | A1 | 1/2021 | Remenschneider et al. | |
| 2021/0204877 | A1 | 7/2021 | Alizadeh-Meghrazi et al. | |
| 2022/0016485 | A1 | 1/2022 | Bissonnette et al. | |
| 2022/0054845 | A1 | 2/2022 | Volpe et al. | |
| 2022/0071489 | A1 * | 3/2022 | Aronoff-Spencer | A61B 5/02444 |
| 2022/0207909 | A1 | 6/2022 | Raguin et al. | |
| 2022/0412857 | A1 | 12/2022 | Fujisaki et al. | |
| 2023/0157564 | A1 | 5/2023 | Zuckerman-Stark et al. | |
| 2024/0016377 | A1 * | 1/2024 | Alleman | A61B 8/4416 |
| 2024/0237916 | A1 | 7/2024 | Ghaednia et al. | |
| 2025/0072791 | A1 * | 3/2025 | Schwab | A61B 9/005 |
| 2025/0275705 | A1 * | 9/2025 | Skrabal | A61B 5/7207 |

FOREIGN PATENT DOCUMENTS

| | | | | |
|---|---|---|---|---|
| CN | 114869345 A | 8/2022 | | |
| CN | 111513692 B | 8/2023 | | |
| FI | 20215783 A1 * | 1/2023 | | G16H 80/00 |
| KR | 10-1728723 B1 | 4/2017 | | |
| WO | 2010054352 A1 | 5/2010 | | |
| WO | 2016178907 A1 | 11/2016 | | |
| WO | 2022/232676 A1 | 11/2022 | | |
| WO | 2022/262669 A1 | 12/2022 | | |
| WO | 2023/158304 A1 | 8/2023 | | |

OTHER PUBLICATIONS

International Search Report and Written Opinion for PCT/US2024/044357 mailed (Applicant—GS-Healthmatrix, LLC) (11 Pages).

International Search Report and Written Opinion for PCT/US2024/044364 mailed Nov. 12, 2024 (Applicant—GS-Healthmatrix, LLC) (14 Pages).

International Search Report and Written Opinion for PCT/US2024/044417 mailed (Applicant—GS-Healthmatrix, LLC) (11 Pages).

International Search Report and Written Opinion for PCT/US2024/044385 mailed Nov. 14, 2024 (Applicant—GS-Healthmatrix, LLC) (12 Pages).

International Search Report and Written Opinion for PCT/US2024/044342 mailed Nov. 15, 2024 (Applicant—GS-Healthmatrix, LLC) (20 Pages).

International Search Report and Written Opinion for PCT/US2024/044404 mailed Nov. 15, 2024 (Applicant—GS-Healthmatrix, LLC) (16 Pages).

Busch, "Reflex Sensors for Telemedicine Applications" SUN Scholar, Mar. 2008, retrieved on [Mar. 11, 2024]. Retrieved from the internet <URL: https://scholar.sun.ac.za/items/93293378-49d9-4530-9bd7-2bc4ed615e6f > entire document.

Zhao. "Ultrasound beam steering with flattened acoustic metamaterial Luneburg lens" Applied Physics Letters; Article [online]. Feb. 18, 2020. [retrieved Oct. 16, 2024]. Retrieved from the Internet: https ://pubs.aip.org/aip/apl/article/116/7 /071902/38294/Ultrasound-beam-steering-with-flattened-acoustic.

Offutt. "Suppression and facilitation of auditory neurons through coordinated acoustic and midbrain stimulation: Investigating a deep brain stimulator for tinnitus" Journal of Neural Engineering; Article [online]. Dec. 2014 [retrieved Oct. 16, 2024]. Retrieved form the Internet: https://pmc.ncbi.nlm.nih.gov/articles/PMC4244264/pdf/nihms-637078.pdf.

Rupin et al. "Mimicking the cochlea with an active acoustic metamaterial" New Journal of Physics; Article [online]. Aug. 2019

(56) References Cited

OTHER PUBLICATIONS

[retrieved Oct. 16, 2024]. Retrieved form the Internet: https://iopscience. iop.org/article/10.1088/1367-2630/ab3d8f/pdf.

* cited by examiner

MULTI-DEVICE HEALTH PARAMETER MONITORING SYSTEMS, METHODS, AND DEVICES

CROSS-REFERENCE TO RELATED APPLICATIONS

This application claims priority to U.S. Provisional Application Ser. No. 63/579,605 filed Aug. 30, 2023 and titled "FRUSTRATED TOTAL INTERNAL REFLECTION (FTIR) SURFACE TOPOGRAPHY AND COMPOSITION ANALYSIS SYSTEMS, METHODS, AND DEVICES;" U.S. Provisional Application Ser. No. 63/579,616 filed Aug. 30, 2023 and titled "SYSTEMS, METHODS, AND DEVICES OF WEARABLE ELECTRO-ACOUSTIC MONITORING;" U.S. Provisional Application Ser. No. 63/579,627 filed Aug. 30, 2023 and titled "SYSTEMS, METHODS, AND DEVICES FOR ACOUSTICALLY ENHANCING IMPLANTS;" U.S. Provisional Application Ser. No. 63/579,633 filed Aug. 30, 2023 and titled SYSTEMS, METHODS, AND DEVICES WITH SENSORS HAVING MULTIPLE DETECTION SIGNAL TYPES;" U.S. Provisional Application Ser. No. 63/579,640 filed Aug. 30, 2023 and titled MULTI-DEVICE HEALTH PARAMETER MONITORING SYSTEMS, METHODS, AND DEVICES;" U.S. Provisional Application Ser. No. 63/579,647 filed Aug. 30, 2023 and titled FRUSTRATED TOTAL INTERNAL REFLECTION (FTIR)-BASED HEALTH PARAMETER DETECTION SYSTEMS, METHODS, AND DEVICES;" and U.S. Provisional Application Ser. No. 63/579,663 filed Aug. 30, 2023 and titled "SYSTEMS, METHODS, AND DEVICES FOR NEUROLOGICAL AND/OR MUSCOSKELETAL PARAMETER CHARACTERIZATION;" the entireties of which are herein incorporated by reference.

BACKGROUND

Current motion tracking systems for virtual reality environments rely on multi-camara arrangements for tracking body motion of the user. These systems are limited in their accuracy/granularity when attempting to assess the user's posture. Moreover, these systems are unable to provide effective direct muscle monitoring.

It is with these observations in mind, among others, that various aspects of the present disclosure were conceived and developed.

SUMMARY

Systems, methods, and devices disclosed herein can address the aforementioned problems. For instance, a health parameter monitoring system can include a platform including a transparent material defining a first measurement surface with one or more light surfaces positioned to provide light into the transparent material and cause a Frustrated Total Internal Reflection (FTIR) event responsive to contact at the first measurement surface. The health parameter monitoring system can also include one or more wearable devices including a base material operable to cover a portion of a human body, an inner surface of the base material defining a second measurement surface, and/or one or more sensors disposed on the base material operable to collect data at the second measurement surface. Additionally, the health parameter monitoring system can include a display; and/or one or more non-transitory storage media storing instructions that, when executed by one or more processors, cause the health parameter monitoring system to present, at the display, locomotion regimen information; collect first health parameter data from the first measurement surface based on the FTIR event; and/or collect second health parameter data from the second measurement surface using the one or more sensors.

In some examples, the display can be a virtual reality headset display. Additionally, the instructions, when executed by the one or more processors, can cause an indicator of data collected at the first measurement surface or the second measurement surface to be presented at the display. The base material can form a sleeve; and/or the second measurement surface can contact a target area on an arm, a leg, or a torso of a subject. Furthermore, the locomotion regimen information can include instructions for a plurality of human body motions; and/or the first health parameter data and the second health parameter data can represent biomechanical information corresponding to the plurality of human body motions. The first health parameter data can be collected with a visible light camera positioned to receive light emitted from the transparent material. Moreover, the one or more sensors can include a plurality of acoustic sensors and a plurality of electrical sensors. Also, the one or more wearable devices can include a plurality of acoustic actuators and a plurality of electrical actuators. The first health parameter data can represent a pressure map formed by feet of a subject positioned on the first measurement surface; and/or the second health parameter data can represent tissue activity data based on an electrical stimulus or an acoustic stimulus generated and detected by the one or more wearable devices.

In some instances, a health parameter monitoring system includes a first measurement surface defined by transparent material forming a platform with one or more light surfaces positioned to provide light into the transparent material and cause a Frustrated Total Internal Reflection (FTIR) event responsive to contact at the first measurement surface. The health parameter monitoring system can include a camera positioned to detect light from the FTIR event; and/or one or more second measurement surfaces defined by one or more inner surfaces of one or more wearable devices. The one or more wearable devices can include one or more sensors operable to collect data at the one or more second measurement surfaces. Furthermore, the health parameter monitoring system can include a computing device including one or more non-transitory storage media storing instructions that, when executed by one or more processors, cause the computing device to collect first health parameter data from the first measurement surface based on the light detected by the camera; and/or collect second health parameter data from the one or more second measurement surfaces using the one or more sensors.

In some scenarios, the health parameter monitoring system can include a display of the computing device operable to present locomotion regimen information including instruction for a plurality of human body motions; and/or one or more indicators of the first health parameter data or the second health parameter data. Additionally, the one or more sensors can include a plurality of acoustic actuators and a plurality of acoustic sensor. The one or more sensors can also include a plurality of electrical actuators and a plurality of electrical sensors. Furthermore, the health parameter monitoring system can include one or more force sensors disposed below the first measurement surface operable to generate force value data responsive to a force applied to the first measurement surface. Moreover, the instructions, when executed by the one or more processors, can cause the computing device to normalize the first health parameter data based on the force value data. The one or more wearable devices can include a plurality of wearable sleeve devices; and/or the one or more second measurement surfaces can include a plurality of second measurement surfaces formed by the plurality of wearable sleeve devices.

In some examples, a method of monitoring health parameters includes collecting first health parameter data at a first measurement surface defined by transparent material forming a platform with one or more light surfaces positioned to provide light into the transparent material and cause a Frustrated Total Internal Reflection (FTIR) event responsive to contact at the first measurement surface; and/or collecting second health parameter data at one or more second measurement surfaces defined by one or more inner surfaces of one or more wearable devices, the one or more wearable devices include one or more sensors operable to measure an electric signal or an acoustic signal at the one or more second measurement surfaces. The method can also include determining a locomotion-related characteristic of a subject based on the first health parameter data and the second health parameter data; and/or causing an indication of the locomotion-related characteristic to be presented at a display of a computing device.

In some instances, collecting the first health parameter data can include receiving, at a camera disposed below the platform, light scattered from the FTIR event. Furthermore, the method can include presenting, at a virtual reality (VR) headset display, locomotion regimen information including instruction for one or more human body motions; and/or detecting the one or more human body motions based on the first health parameter data and the second health parameter data. Determining the locomotion-related characteristic can include determining a pressure distribution based on the first health parameter data; and/or determining a muscle activation or a nerve activation based on the second health parameter data.

BRIEF DESCRIPTION OF THE DRAWINGS

The foregoing summary, as well as the following detailed description, will be better understood when read in conjunction with the appended drawings. For the purpose of illustration, there is shown in the drawings certain embodiments of the disclosed subject matter. It should be understood, however, that the disclosed subject matter is not limited to the precise embodiments and features shown. The accompanying drawings, which are incorporated in and constitute a part of this specification, illustrate an implementation of systems and methods consistent with the disclosed subject matter and, together with the description, serves to explain advantages and principles consistent with the disclosed subject matter, in which.

DETAILED DESCRIPTION

Figure 1:
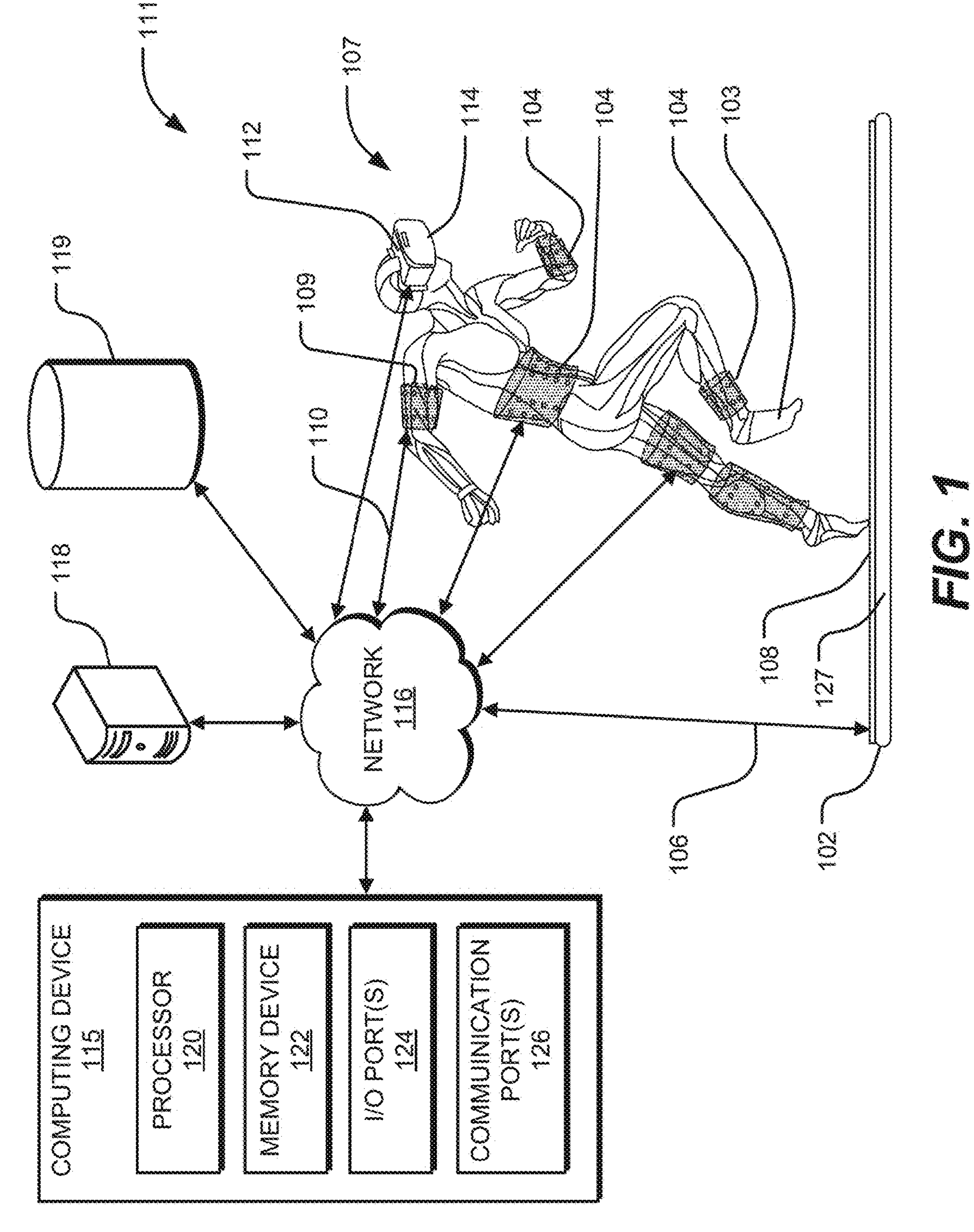
FIG. 1 illustrates an example system for health parameter monitoring using multiple data collection devices.

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other instances, methods, procedures and components have not been described in detail so as not to obscure the related relevant feature being described. Also, the description is not to be considered as limiting the scope of the embodiments described herein. The drawings are not necessarily to scale and the proportions of certain parts may be exaggerated to better illustrate details and features of the present disclosure.

The phraseology and terminology employed herein are for the purpose of description and should not be regarded as limiting. For example, the use of a singular term, such as, “a” is not intended as limiting of the number of items. Also, the use of relational terms such as, but not limited to, “top,” “bottom,” “left,” “right,” “upper,” “lower,” “down,” “up,” and “side,” are used in the description for clarity in specific reference to the figures and are not intended to limit the scope of the presently disclosed technology or the appended claims. Further, it should be understood that any one of the features of the presently disclosed technology may be used separately or in combination with other features. Other systems, methods, features, and advantages of the presently disclosed technology will be, or become, apparent to one with skill in the art upon examination of the figures and the detailed description. It is intended that all such additional systems, methods, features, and advantages be included within this description, be within the scope of the presently disclosed technology, and be protected by the accompanying claims.

Further, as the presently disclosed technology is susceptible to embodiments of many different forms, it is intended that the present disclosure be considered as an example of the principles of the presently disclosed technology and not intended to limit the presently disclosed technology to the specific embodiments shown and described. Any one of the features of the presently disclosed technology may be used separately or in combination with any other feature. References to the terms “embodiment,” “example,” and/or the like in the description mean that the feature and/or features being referred to are included in, at least, one aspect of the description. Separate references to the terms “examples,” “embodiments,” and/or the like in the description do not necessarily refer to the same embodiment and are also not mutually exclusive unless so stated and/or except as will be readily apparent to those skilled in the art from the description. For instance, a feature, structure, process, step, action, or the like described in one embodiment may also be included in other embodiments but is not necessarily included. Thus, the presently disclosed technology may include a variety of combinations and/or integrations of the examples described herein. Additionally, all aspects of the present disclosure, as described herein, are not essential for its practice. Likewise, other systems, methods, features, and advantages of the presently disclosed technology will be, or become, apparent to one with skill in the art upon examination of the figures and the description. It is intended that all such additional systems, methods, features, and advantages be included within this description, be within the scope of the presently disclosed technology, and be encompassed by the claims.

Any term of degree such as, but not limited to, "substantially," as used in the description and the appended claims, should be understood to include an exact, or a similar, but not exact configuration. For example, "a substantially planar surface" means having an exact planar surface or a similar, but not exact planar surface. Similarly, the terms "about" or "approximately," as used in the description and the appended claims, should be understood to include the recited values or a value that is three times greater or one third of the recited values. For example, about 3 mm includes all values from 1 mm to 9 mm, and approximately 50 degrees includes all values from 16.6 degrees to 150 degrees.

The term "coupled" is defined as connected, whether directly or indirectly through intervening components, and is not necessarily limited to physical connections. The connection can be such that the objects are permanently connected or releasably connected. The terms "comprising," "including" and "having" are used interchangeably in this disclosure. The terms "comprising," "including" and "having" mean to include, but not necessarily be limited to the things so described. The term "real-time" or "real time" means substantially instantaneously.

Lastly, the terms "or" and "and/or," as used herein, are to be interpreted as inclusive or meaning any one or any combination. Therefore, "A, B, or C" or "A, B, and/or C" mean any of the following: "A," "B," or "C"; "A and B"; "A and C"; "B and C"; "A, B and C." An exception to this definition will occur only when a combination of elements, functions, steps or acts are in some way inherently mutually exclusive.

The systems, methods, and devices disclosed herein bring together multiple, different types of sensor systems to improve the health parameter monitoring of a subject. The devices can include a standing platform which uses Frustrated Total Internal Reflection (FRIT) to measure a pressure distribution, a blood perfusion distribution, a 3D surface topography, and/or other physical or physiological traits of the subject on the standing platform. Additionally or alternatively, the system can include various wearable devices that include electro-acoustic sensors and actuators to stimulate and/or measure soft tissue activity at a target area of the subject (e.g., a muscle, a nerve, and/or a tendon). Collection and utilization of this data while the subject is interacting with a Virtual Reality (VR) environment via a VR headset can improve the health parameter analysis capabilities of the system, as discussed herein. This technology can be used in gaming, sports, physical rehabilitation, and/or military training. Moreover, technology disclosed herein can be combined with one or multiple screens or VR screens or headsets to expose subjects or gamers to specific experiences or interactions, which can instruct the user to perform various body motions.

Furthermore, the systems, methods, and devices disclosed herein can provide pressure maps of the subject's footprint and/or body tissue activity measurements for better understanding of the subject's posture. The technology disclosed herein can be used for improved direct muscle monitoring to create a better understanding of muscle activation patterns and how these patterns correspond to particular body motions. Moreover, the collected data can be presented in real-time to show a mapping of the measured parameters on a digital mapping of the subject's body. For example, a gamer in a VR video game trying to pick up a heavy object could have their muscle activity and/or posture tracked to determine if the muscles of the subject are contracted enough or not.

Additional benefits and advantages of the presently disclosed technology will become apparent from the detailed description below.

FIG. 1. depicts an example health parameter monitoring system 100 with multiple, simultaneous data collection devices including an FTIR-based platform 102 and/or one or more wearable device(s) 104. The FTIR-based platform 102 can collect first health parameter data 106 representing physical and/or physiological characteristics of a subject 107 based on their foot's 103 contact with a first measurement surface 108 of the FTIR-based platform 102. The wearable device(s) 104 can define a second measurement surface 109 to collect second health parameter data 110 representing other physical and/or physiological characteristics of the subject 107, or a particular target region of the subject 107 (e.g., a muscle or a nerve). The FTIR-based platform 102 is discussed in greater detail below regarding FIGS. 2 and 3 and the wearable device(s) 104 are discussed in greater detail below regarding FIG. 4.

In some examples, the health parameter monitoring system 100 can include a display device 112, such as a VR headset 114. The VR headset 114 can be worn by the subject 107 during a data collection procedure 111, for instance, to present locomotion regimen information at a display of the VR headset 114. The locomotion regimen information can include instructions to the subject 107 to perform various motions with their body (e.g., stand, walk, run, squat, stand on one leg, lean, perform an action with a virtual object, and so forth). The locomotion regimen information can include an exercise application, a physical therapy application, a video game, a video, a song, text, and/or combinations thereof. Additionally or alternatively, the VR headset 114 can present information based on the first health parameter data 106 and/or the second health parameter data 110, such as various indicators of the physiological characteristics being measured (e.g., a pressure distribution map, a run speed, or so forth).

In some examples, the FTIR-based platform 102, the wearable device(s) 104, and/or the VR headset 114 can transmit the data they generate to one or more computing device 115. The computing device 115 can be an additional separate device, and/or the computing device 115 can be formed into one of the other devices (e.g., the FTIR-based platform 102, the wearable device(s) 104), and/or the VR headset 114). The computing device 115 can receive and/or transmit data to and from the other components of the health parameter monitoring system 100 using a network 116 (e.g., using one or more network connections). The network 116 can include any type of network, such as the Internet, an intranet, a Virtual Private Network (VPN), a Voice over Internet Protocol (VoIP) network, a wireless network (e.g., Bluetooth), a cellular network (e.g., 4G, 5G, LTE, etc.), satellite, combinations thereof, etc. The network 116 can include communications network(s) with numerous components such as, but not limited to gateways routers, servers, and registrars, which enable communication across the network 116. In one implementation, the communications network(s) includes multiple ingress/egress routers, which may have one or more ports, in communication with the network 116. Additionally, or alternatively, the FTIR-based platform 102, the wearable device(s) 104, and/or the VR headset 114 can access and be accessed by the network 116 via another type of communications network, which may be a public switched telephone network (PSTN) operated by a local exchange carrier (LEC) and/or a wireless network.

The health parameter monitoring system 100 can also include at least one server 118 hosting a website or application that the FTIR-based platform 102, the wearable device(s) 104, and/or the VR headset 114 may visit to access the health parameter monitoring system 100. The server 118 can access (e.g., read and/or write) one or more database(s) 119. The website or application can receive the inputs from the FTIR-based platform 102, the wearable device(s) 104, the VR headset 114, and/or other computing devices 115, and can analyze the inputs to generate outputs for the health parameter monitoring system 100 (e.g., which can be stored at the database(s) 119). The server 118 may be a single server, a plurality of servers with each such server being a physical server or a virtual machine, or a collection of both physical servers and virtual machines. In another implementation, a cloud hosts one or more components of the health parameter monitoring system 100. The server 118 may represent an instance among large instances of application servers in a cloud computing environment, a data center, or other computing environment. The server 118 can access the data stored at the one or more database(s) 119. The FTIR-based platform 102, the wearable device(s) 104, the VR headset 114, and/or other resources connected to the network 116 may access one or more other servers to access one or more websites, applications, web services interfaces, storage devices, computing devices, or the like, thus providing the health parameter monitoring system 100.

In some instances, the computing device(s) 115 can include a computer, a personal computer, a desktop computer, a laptop computer, a terminal, a workstation, a cellular or mobile phone, a mobile device, a smart mobile device, a tablet, a wearable device (e.g., a smart watch, smart glasses, a smart epidermal device, etc.), a multimedia console, a television, an Internet-of-Things (IoT) device, a smart home device, another virtual reality (VR) or augmented reality (AR), and/or the like. It will be appreciated that specific implementations of these devices may be of differing possible specific computing architectures.

The computing device 115 may be a computing system capable of executing a computer program product to execute a computer process. Data and program files may be input to the computing device 115, which reads the files and executes the programs therein. Some of the elements of the computing device 115 can include one or more hardware processors 120, one or more memory devices 122, and/or one or more ports, such as input/output (IO) port(s) 124 and communication port(s) 126. Various elements of the computing device 115 may communicate with one another by way of the communication port(s) 126 and/or one or more communication buses, point-to-point communication paths, or other communication means.

The processor 120 may include, for example, a central processing unit (CPU), a microprocessor, a microcontroller, a digital signal processor (DSP), a graphics processing unit (GPU), and/or one or more internal levels of cache. There may be one or more processors 120, such that the processor 120 comprises a single central-processing unit, or a plurality of processing units capable of executing instructions and performing operations in parallel with each other, commonly referred to as a parallel processing environment.

The computing device 115 may be a single computer, a plurality of computers (e.g., a distributed computer), or any other type of computer, such as one or more external computers made available via a cloud computing architecture. The presently described technology is optionally implemented in software stored on the data storage device(s) such as the memory device(s) 122, and/or communicated via one or more of the ports 124/126 to the FTIR-based platform 102, the wearable device(e) 104, and/or the VR headset 114, thereby transforming the computing device 115 to a special purpose machine for implementing the operations described herein.

The one or more memory device(s) 122 may include any non-volatile data storage device capable of storing data generated or employed within the computing device 115, such as computer executable instructions for performing a computer process, which may include instructions of both application programs and an operating system (OS) that manages the various components of the computing device 115. The memory device(s) 122 may include, without limitation, magnetic disk drives, optical disk drives, solid state drives (SSDs), flash drives, and the like. The memory device(s) 122 may include removable data storage media, non-removable data storage media, and/or external storage devices made available via a wired or wireless network with such computer program products, including one or more database management products, web server products, application server products, and/or other additional software components. Examples of removable data storage media include Compact Disc Read-Only Memory (CD-ROM), Digital Versatile Disc Read-Only Memory (DVD-ROM), magneto-optical disks, flash drives, and the like. Examples of non-removable data storage media include internal magnetic hard disks, SSDs, and the like. The one or more memory device(s) 122 may include volatile memory (e.g., dynamic random-access memory (DRAM), static random-access memory (SRAM), etc.) and/or non-volatile memory (e.g., read-only memory (ROM), flash memory, etc.).

Computer program products containing mechanisms to effectuate the systems and methods in accordance with the presently described technology may reside in the memory device(s) 122 which may be referred to as machine-readable media. It will be appreciated that machine-readable media may include tangible non-transitory medium capable of storing or encoding instructions to perform operations of the health parameter monitoring system 100. The machine-readable media can store computer-readable instructions for execution by a machine, and/or can be capable of storing or encoding data structures and/or modules utilized by or associated with such instructions.

In some implementations, the computing device 115 includes one or more ports, such as the I/O port 124 and the communication port 126, for communicating with other computing, network, or devices. It will be appreciated that the I/O port 124 and the communication port 126 may be combined or separate and that more or fewer ports may be included in the computing device 115.

The I/O port 124 may be connected to an I/O device, or other device, by which information is input to or output from the computing device 115. Such I/O devices may include, without limitation, one or more input devices and/or output devices. The input devices can convert a human-generated signal, such as, human voice, physical movement, physical touch or pressure, and/or the like, into electrical signals as input data into the computing device 115 via the I/O port 124. Similarly, the output devices may convert electrical signals received from the computing device 115 via the I/O port 124 into signals that may be sensed as output by a human, such as sound, light, and/or touch. The input device may be an alphanumeric input device, including alphanumeric and other keys for communicating information and/or command selections to the processor 120 via the I/O port 124. The input device may be another type of user input device including, but not limited to: direction and selection control devices, such as a mouse, a trackball, cursor direction keys, a joystick, and/or a wheel; one or more sensors, such as a camera, a microphone, a positional sensor, an orientation sensor, an inertial sensor, an accelerometer; and/or a touch-sensitive display screen ("touchscreen"). The output devices may include, without limitation, a display, a touchscreen, a speaker, a tactile or haptic output device, and/or the like. In some implementations, the input device and the output device may be the same device, for example, in the case of a touchscreen.

In one implementation, the communication port 126 is connected to the network 116, and the computing device 115 may receive network data useful in executing the methods and systems set out herein as well as transmitting information and network configuration changes determined thereby. Stated differently, the communication port 126 can connect the computing device 115 to one or more communication interface devices configured to transmit and/or receive information between the computing device 115 and other devices by way of one or more wired or wireless communication networks or connections. Examples of such networks connections include, without limitation, Universal Serial Bus (USB), Ethernet, Wi-Fi, Bluetooth®, Near Field Communication (NFC), and so on. One or more such communication interface devices may be utilized via the communication port 126 to communicate with one or more other machines, either directly over a point-to-point communication path, over a wide area network (WAN) (e.g., the Internet), over a local area network (LAN), over a cellular network (e.g., third generation (3G), fourth generation (4G), Long-Term Evolution (LTE), fifth generation (5G), etc.) or over another communication means. Further, the communication port 126 may communicate with an antenna or other link for electromagnetic signal transmission and/or reception.

Operations of the health parameter monitoring system 100 and various methods disclosed herein performed by the health parameter monitoring system 100 may be embodied as data structures and/or instructions stored on the memory devices 122 and executed by the processor 120. For instance, the methods and operations disclosed may be implemented as sets of instructions that are software-readable by the computing device 115.

Figure 2:
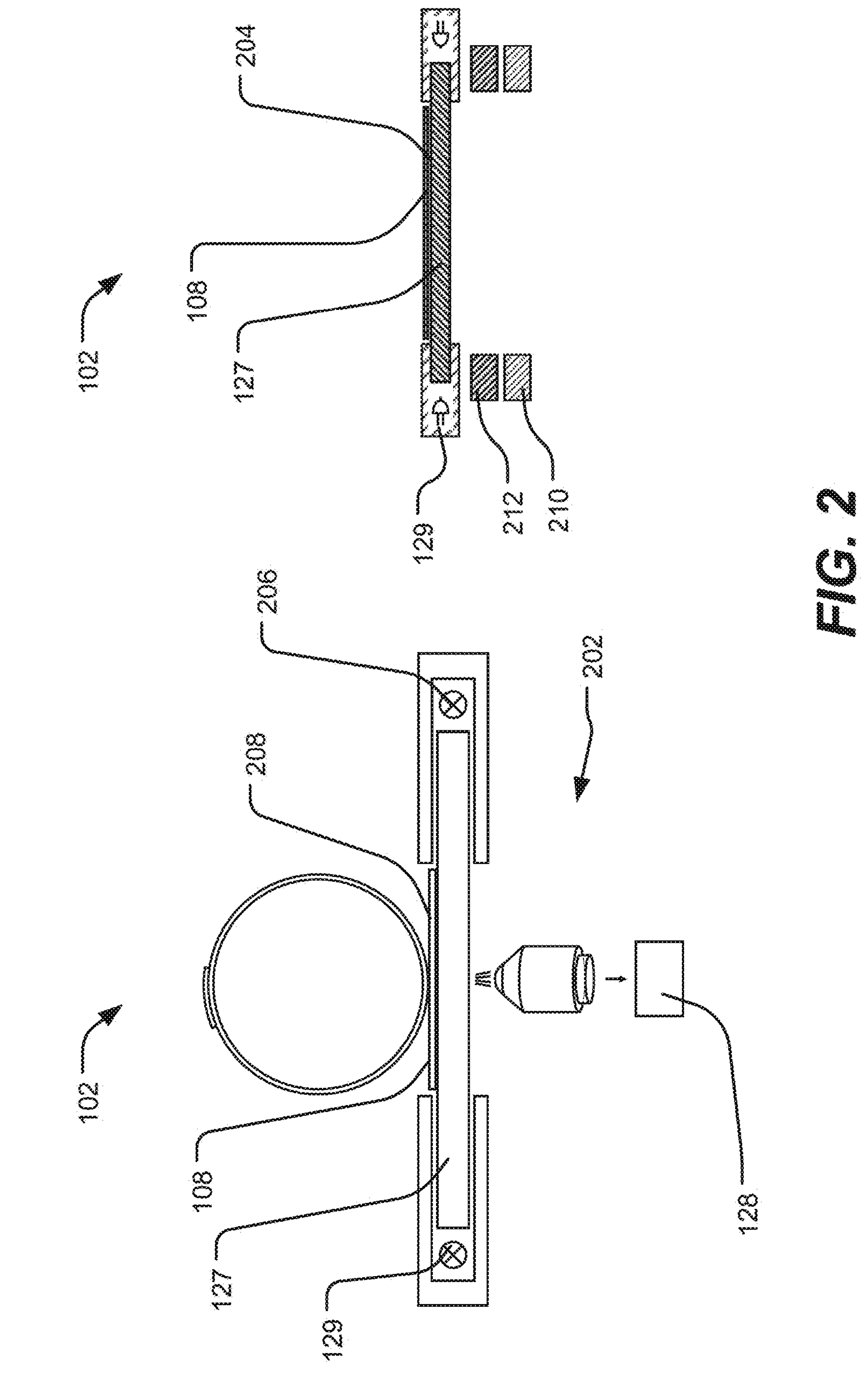
FIG. 2 illustrates an example system for health parameter monitoring including at least a Frustrated Total Internal Reflection (FTIR)-based platform.

FIG. 2 illustrates an example health parameter monitoring system 100 including the FTIR-based platform 102 for generating the first health parameter data 106. The system(s) 100 depicted in FIG. 2 can form at least a portion of the system 100 depicted in FIG. 1. The FTIR-based platform 102 can be a scanning device 202 which uses a transparent material 127 (e.g., a glass sheet) to trap electromagnetic waves while a subject 107 is standing on a flat surface 204 of the transparent material (e.g., the first measurement surface). A camera 128 on another side of the glass sheet (e.g., a side surface adjacent the glass sheet or below the glass sheet opposite the first measurement surface) can record the photons scattered due to an FTIR event. An amount of scattered light detected by the camera 128 can correspond to an amount of surface contact and/or an amount of pressure applied to the glass sheet by the subject 107. Furthermore, the LEDs 129 with different wavelengths can be turned on one-by-one (e.g., in a sequence), for instance, from smaller wavelengths to larger wavelengths or vice versa. The camera 128 can record the scattered photos at the different LED illumination stage to record slices of the contacting area at different distances to the glass surface. The different distances from the glass surface at which light scatters correspond to the different wavelengths of the LEDs. By combining these pictures, a 3D surface topography of the contact area can be generated. Moreover, a particular set of LEDs having a particular combination of frequencies can be illuminated to generate the 3D surface topology. From the 3D surface topology, a physical and/or physiological parameter of the skin surface, the foot, and/or the subject 107 can be determined. For instance, the 3D surface topology can be assessed to determine a roughness factor or a friction factor, for instance, based on a smoothness/uniformity of the 3D surface topology. Additionally, various anatomical features under the surface of the skin (e.g., muscles veins, tendons, or so forth) can also be detected and/or identified by the 3D surface topology.

Moreover, the technology disclosed herein can provide information about the material composition of the contacting skin surface. FTIR spectroscopy for determining the material composition can be performed simultaneously with generating the 3D surface topology. One or more visible light cameras 128 can detect electromagnetic waves emitted one-by-one and only at the wavelengths needed for the material composition analysis. Moreover, a particular set of LEDs having a particular combination of frequencies can be illuminated for a particular material spectroscopy analysis. For example, if the FTIR-based platform 102 is used to check the oxygen level at the contact surface, LEDs 129 that emit certain wavelengths of EM waves for detecting oxygen can be used (e.g., between 1400-1600 nm). In some examples, the chemical composition analysis performed with the camera 128 and multiple different wavelengths is an improvement over other FTIR spectroscopy devices that may use light spectrometers.

In some examples, the plurality of LEDs 129 can be arranged in a strip or array inside the FTIR-based platform 102. Moreover, the FTIR-based platform 102 can include one or more interchangeable LED assemblies 206 that correspond to a particular use case, a particular component of the material composition, and so forth. The glass medium can also have an electrically conductive portion, such as transparent, electrically conducting ink 208, formed onto the contact surface of the glass sheet, which can send and/or receive an electrical signal to the contact area of the subject 107. Furthermore, other portions of the transparent medium 127 can be covered with a shield, paint, or other opaque material to trap the photons in the transparent medium 127. The FTIR-based platform 102 can include one or more force sensors 210 to collect force data from the first measurement surface 108, and/or one or more acoustic sensors/actuators 212 (e.g., to detect or send an acoustic signal from the subject's feet 109). Furthermore, any type of pressure mapping or force plate platforms could be used in addition to or alternatively to the FTIR-based sensing portions.

Figure 3:
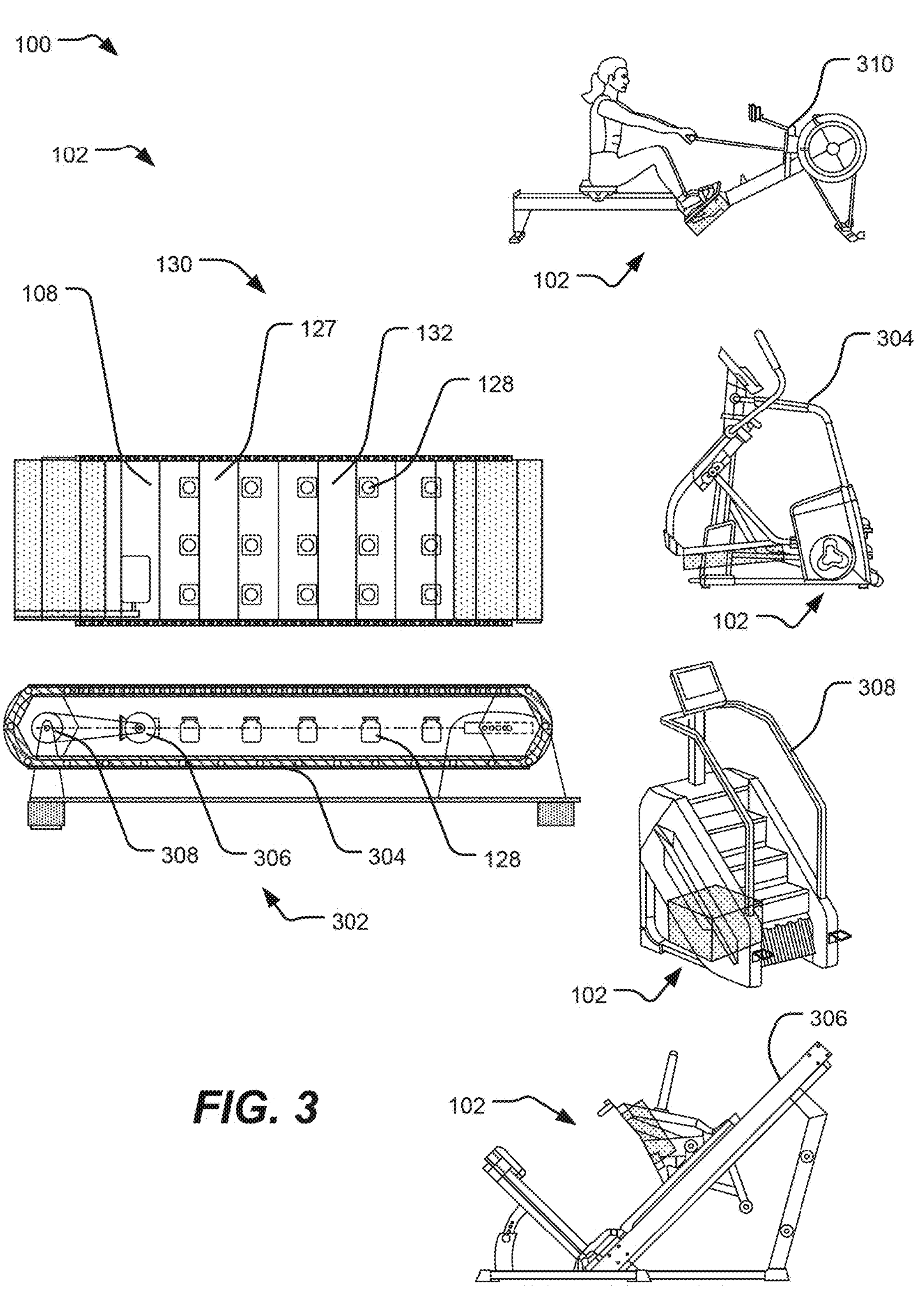
FIG. 3 illustrates an example system for health parameter monitoring including at least a dynamic motion measurement device with an FTIR-based platform.

FIG. 3 depicts an example FTIR-based platform 102 which can be integrated into a dynamic movement measurement device 302. The system(s) 100 depicted in FIG. 3 can form at least a portion of the system 100 depicted in FIG. 1. The FTIR-based platform 102 can be integrated into a dynamic or moving machine such as an exercise machine, a physical therapy machine, or another locomotion type of machine. These machines can provide improved spatial resolution for measuring health parameters, such that data can be captured corresponding to particular movements which can be performed repetitively over a period of time (e.g., multiple minutes). By way of example, the dynamic measurement device can be an exercise or physical therapy device, such as a treadmill machine 130, an elliptical machine 304, a leg press 306, a stair stepping machine 308, and/or a row machine 310, incorporating the FTIR-based platform 102. Additionally, a particular motion of the dynamic movement measurement device can be presented as locomotion regime information, such as a virtual representation in a VR video game (e.g., rowing a boat, climbing stairs, and so forth).

In some instances, the dynamic movement measurement device 302 can be a treadmill machine 130 which traps light from the plurality of LEDs 129 inside a flexible running belt 132 formed of the transparent medium 127, which the subject 107 moves on (e.g., standing, walking, and/or running). Multiple cameras 128 can record footprints causing pressure and/or FTIR events on the transparent medium 127, and then a processing unit 120 can transform the footprints to pressure maps. Additionally or alternatively, the treadmill machine 130 can include a rigid deck which includes the transparent material 127 of the FTIR-based platform 102, with the flexible running belt 132 layered over the rigid deck. Moreover, the treadmill machine 130 can include a plurality of planks or bars 304 forming a continuous track of transparent material 127. Furthermore, the treadmill machine 130 can include one or more motors 306 connected to one or more rollers 308 for generating rotational motion for the one or more rollers 308. The treadmill machine 130 can also include a frame to which the other components are fastened/mounted. The flexible running belt 132 and/or the continuous track can wrap around the one or more rollers. Furthermore, the treadmill machine 130 can include an incline mechanism for adjusting a height dimension at one side of the treadmill machine 130, and a belt fastening mechanism for fastening the flexible running belt 132 in place. Furthermore, the treadmill machine 130 can include the one or more cameras 128, such as a plurality or array of cameras 128 in an interior portion of the treadmill machine 130 directed up towards the transparent medium 127. Additionally, the treadmill machine 130 can include one or more light sources, such as the plurality of LEDs 129 for providing light into the flexible running belt 132.

Figure 4:
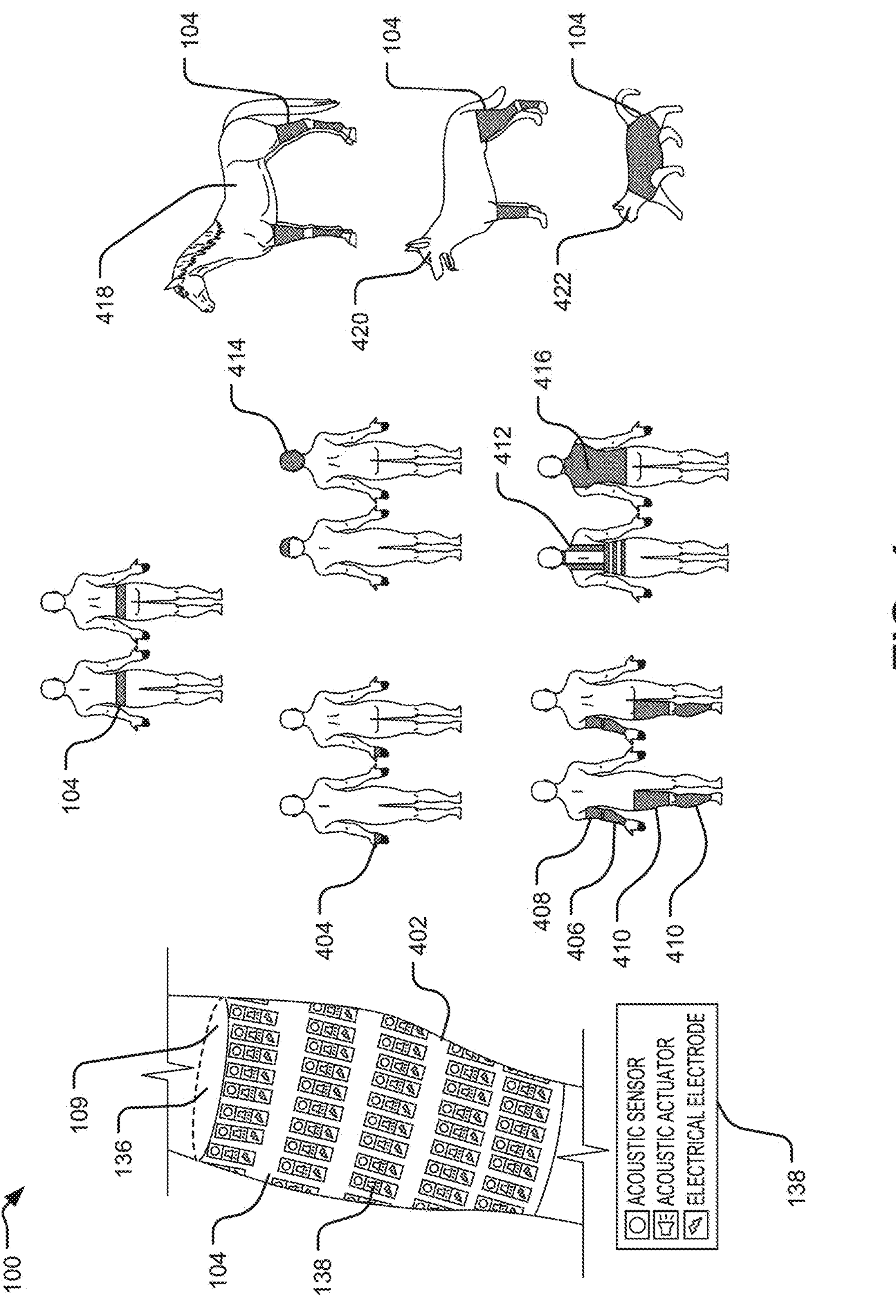
FIG. 4 illustrates an example system for health parameter monitoring including at least a wearable device.

FIG. 4 depicts an example health parameter monitoring system 100 including various configurations of the wearable device(s) 104. The system(s) 100 depicted in FIG. 4 can form at least a portion of the system 100 depicted in FIG. 1.

In some examples, the wearable device(s) 104 disclosed herein can be capable of independent acoustic and electrical sensing and actuating, simultaneously. At the same time, these wearable device(s) 104 can be used to stimulate the body in one of the electrical domain or the acoustic domain and monitor the reaction of the body using the other domain. The wearable device(s) 104 can include an inner surface 136 that forms the second measurement surface 109 for collecting the second health parameter data 110 (e.g., acoustic data and/or electrical data).

In some instances, the second health parameter data 110 collected with the wearable device(s) 104 can be used for a variety of physical and/or physiological assessments, which can be performed simultaneously with the generation and/or presentation of the first health parameter data 106 from the FTIR-based platform 102. For instance, the wearable device (s) 104 can be used to perform one or more of an acoustic stimulation procedure; an acoustic diagnostics and/or monitoring procedure; an electrical mythography procedure; an electrical impedance tomography procedure; an electro-acoustic neuromodulation procedure; an electro-acoustic muscle characterization procedure; and/or combinations thereof.

Accordingly, the wearable device(s) 104 disclosed herein can have a variety of uses for different target regions of the user. The wearable device can be used to monitor muscle activity, muscle health, and a muscle healing process. Additionally, the health parameter monitoring system 100 disclosed herein can be used to monitor bone density, water content, and a bone healing process with the wearable device(s) 104. The health parameter monitoring system 100 can also monitor an implant healing process and/or perform a diagnosis of a defect in implant fixation.

In some examples, the wearable device(s) 104 can be formed of fabric, plastic, or other flexible or partially flexible materials and/or various other types of material to form different shapes, sizes, and form-factors. The wearable device 104 can also include one or more sensors and/or actuators, such as a plurality of sensors/actuators 138. The plurality of sensors/actuators 138 can include any combination of acoustic actuators, acoustic sensors, electrical actuators, and/or electrical sensors. The wearable device 104 can include one or more integrated sensors/actuators, the integrated sensor/actuator being a combination of the acoustic sensor, the acoustic actuator, and/or the electrical electrode. The wearable device(s) 104 can include an array of the integrated sensors. The wearable(s) device 104 can also include a power source, such as a battery and/or an AC power adapter disposed on the wearable device(s) 104 (or separate from the wearable device(s) 104). The wearable device(s) 104 can also include a controller, such as a processor 120 or microcontroller, for implementing a sensing control system, an actuation control system, and/or a sensing analytics engine. The controller and/or any components of the controller can be integral with the wearable device(s) 104 (e.g., disposed on the wearable device(s) 104), or the controller and/or any components of the controller can be remote or separate from the wearable device(s) 104, as discussed above. The sensing analytics engine can perform one or more sensor data analyses and/or cross-domain analyses 502 using the sensor data.

In some instances, the acoustic-electric wearable device (s) 104 can generate acoustic and electrical signals with different waveforms (e.g., pure tone, gaussian waves, or so forth), different frequencies (e.g., 1 Hz to 10 MHz), and/or different intensities. The generated signals can interact with soft and hard tissues. These interactions may lead to transformation of tissues or transformation of waves. The transformed waves can be measured using the same or a different array of electrical and acoustic sensors. Furthermore, the plurality of sensors/actuators 138 can include one or more piezoelectric transducer used for momentous sensing and actuating, and/or one or more micro-electromechanical system (MEMS) microphones and/or speakers, which can be used for denser arrays. The wearable device(s) 104 can also include a small-scale FTIR-based sensor and/or any of the components of the FTIR-based platform 102 formed as a micrometer, millimeter, or centimeter scale sensor assembly on the base material of the wearable device(s) 104. The sensing analytics engine can include one or more machine learning (ML) models for extracting information from the acoustic, electrical, thermal, and/or optical signals measured at the wearable device(s) 104, for instance, using various architectures to perform a time series analysis).

In some examples, the wearable device(s) 104 can form one or more cuffs or sleeves 402 configured to at least partially cover and/or wrap around particular target areas or regions of the body. For example, the wearable device(s) 104 can include one or more of a hand sleeve 404, a wrist sleeve 406, an arm sleeve 408 (e.g., an upper arm sleeve and/or a lower arm sleeve), a leg sleeve 410 (e.g., an upper leg sleeve and/or a lower leg sleeve), a torso band 412, a head cap 414, a back strap 416, a chest strap, a back harness, and/or any combinations thereof. Furthermore, in scenarios where the health parameter monitoring system 100 is used for animal husbandry, the wearable device(s) 104 can form an animal leg sleeve and/or a body harness operable for use with a horse 418, a dog 420, a cat 422, or so forth.

In some examples, an acoustic signal and/or an electrical signal from the wearable device(s) 104 can be detected at the FTIR-based platform 102 directly and/or via a response at the first measurement surface 108. Moreover, a signal actuation (e.g., an acoustic signal, an electrical signal, an optical signal, and/or a thermal signal) generated at the FTIR-based platform 102 can be detected at the wearable device(s) 104 directly and/or via a biological response at the target region (e.g., a muscle response or a nerve response) measured by the second measurement surface 109.

Figure 5:
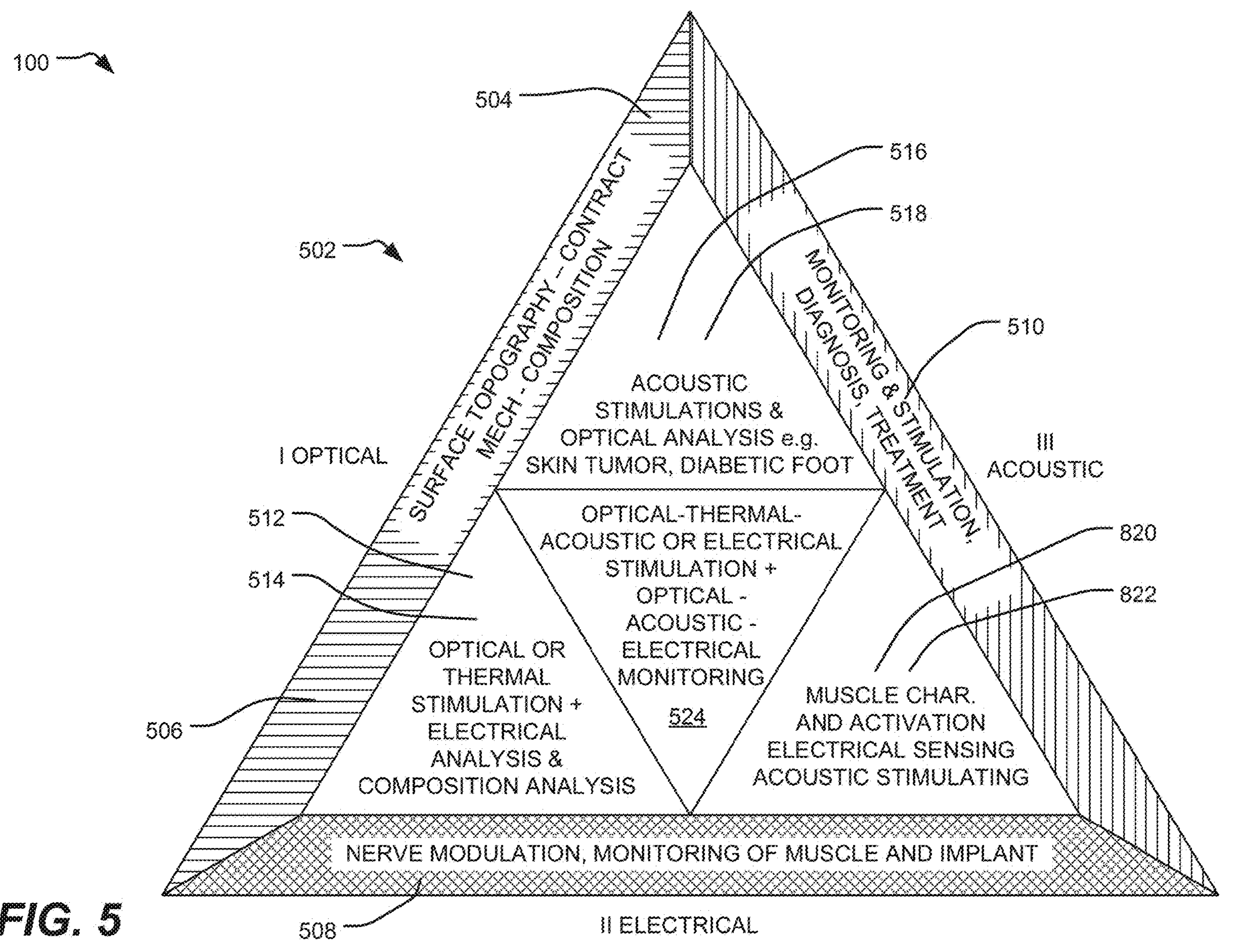
FIG. 5 illustrates an example system for health parameter monitoring including at least a cross-domain data analysis.

FIG. 5 illustrates an example diagram 501 of multi-device, multi-signal type analyses 504 (e.g., the cross-domain analyses 502) which can be performed by the systems 100 depicted herein. The system(s) 100 depicted in FIG. 5 can form at least a portion of the system 100 depicted in FIG. 1. The diagram depicted in FIG. 5 shows how different combinations of signals from the FTIR-based platform 102 and/or the wearable device(s) 104 can be used for different sensing and analytics procedures. For example, FIG. 5 shows how two, three, or four different signal types (e.g., optical 506, electrical 508, acoustic 510, and/or thermal) can be integrated into a cross-domain analysis 504. For example, the optical sensing/actuating modality 506 can be used for determining a surface topology, contact mechanics of the surface (e.g., friction, roughness, slippage), and/or surface composition. The electrical sensing/actuating modality 508 can be used for nerve modulation, monitoring of muscle activity, and/or detecting implant characteristics. The acoustic sensing/actuating modality 510 can include monitoring or stimulation of muscle, bone, and/or tendon tissue, blood flow, combinations thereof, and/or diagnosis/treatments. When combined into a two-signal cross-domain analysis, the optical sensing/actuating modality 506 can combine with the electrical sensing/actuating modality 508 to perform optical or thermal stimulations 512 with electrical analysis and/or composition analysis 514. When combined into a two-signal cross-domain analysis, the optical sensing/actuating modality 506 can combine with the acoustic sensing/actuating modality 510 to perform acoustic stimulations 516 with optical analysis 518 (e.g., for skin tumor analysis, diabetic foot analysis, etc.). When combined into a two-signal cross-domain analysis, the acoustic sensing/actuating modality 510 can combine with the electrical sensing/actuating modality 508 to perform muscle characterization and activation 520 with electrical sensing and/or acoustic stimulation 522. When combined into a three or four-signal cross-domain analysis 524, the optical, electrical, acoustic, and/or thermal sensing/actuating modalities can be combined for optical-thermal-acoustic and/or electrical stimulation with optical-acoustic-electrical and/or thermal monitoring, which can be used to inform any of the functionalities discussed herein.

Figure 6:
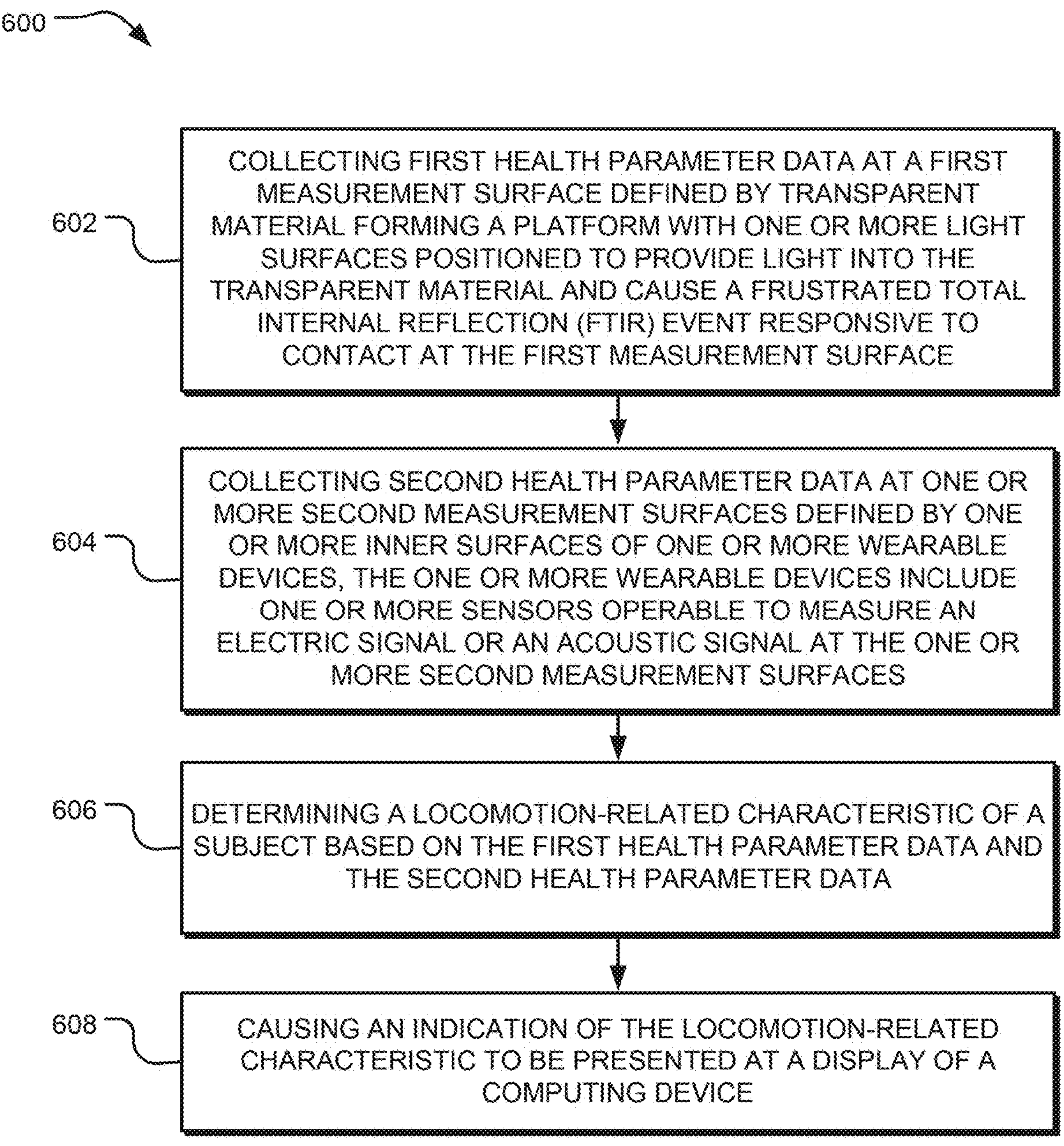
FIG. 6 illustrates an example method which can be performed by any of the systems depicted in FIGS. 1-5.

FIG. 6 depicts an example method 600 for monitoring one or more health parameters. The method 600 can be performed by any of the systems 100 depicted herein.

In some examples, at operation 602, the method 600 can collect first health parameter data at a first measurement surface defined by transparent material forming a platform with one or more light surfaces positioned to provide light into the transparent material and cause a Frustrated Total Internal Reflection (FTIR) event responsive to contact at the first measurement surface. At operation 604, the method 600 can collect second health parameter data at one or more second measurement surfaces defined by one or more inner surfaces of one or more wearable devices, the one or more wearable devices include one or more sensors operable to measure an electric signal or an acoustic signal at the one or more second measurement surfaces. At operation 606, the method 600 can determine a locomotion-related characteristic of a subject based on the first health parameter data and the second health parameter data. At operation 608, the method 600 can cause an indication of the locomotion-related characteristic to be presented at a display of a computing device.

It is to be understood that the specific order or hierarchy of steps in the method(s) depicted throughout this disclosure are instances of example approaches and can be rearranged while remaining within the disclosed subject matter. For instance, any of the operations depicted throughout this disclosure may be omitted, repeated, performed in parallel, performed in a different order, and/or combined with any other of the operations depicted throughout this disclosure.

While the present disclosure has been described with reference to various implementations, it will be understood that these implementations are illustrative and that the scope of the present disclosure is not limited to them. Many variations, modifications, additions, and improvements are possible. More generally, implementations in accordance with the present disclosure have been described in the context of particular implementations. Functionality may be separated or combined differently in various implementations of the disclosure or described with different terminology. These and other variations, modifications, additions, and improvements may fall within the scope of the disclosure as defined in the claims that follow.

What is claimed is:

1. A health parameter monitoring system comprising:

a platform including a transparent material defining a first measurement surface with one or more light surfaces positioned to provide light into the transparent material and cause a Frustrated Total Internal Reflection (FTIR) event responsive to contact at the first measurement surface;

one or more wearable devices including:

a base material operable to cover a portion of a human body, an inner surface of the base material defining a second measurement surface, and one or more sensors disposed on the base material operable to collect data at the second measurement surface, the second measurement surface contacts a target area on an arm, a leg, or a torso of a subject, and the one or more sensors include at least an acoustic actuator and an acoustic sensor;

a display; and one or more non-transitory storage media storing instructions that, when executed by one or more processors, cause the health parameter monitoring system to:

present, at the display, locomotion regimen information;

collect first health parameter data from the first measurement surface based on the FTIR event; and collect second health parameter data from the second measurement surface using the one or more sensors, the second health parameter data represents tissue activity data detected by at least one of:

the acoustic sensor using an acoustic stimulus from the acoustic actuator to the target area or using an electrical stimulus at the target area; or an electrical sensor using the acoustic stimulus from the acoustic actuator to the target area or using the electrical stimulus at the target area.

2. The system of claim 1, wherein, the display is a virtual reality headset display.

3. The system of claim 2, wherein, the instructions, when executed by the one or more processors, cause an indicator of data collected at the first measurement surface or the second measurement surface to be presented at the display.

4. The system of claim 3, wherein, the base material forms a sleeve.

5. The system of claim 1, wherein, the locomotion regimen information includes instruction for a plurality of human body motions; and the first health parameter data and the second health parameter data represent biomechanical information corresponding to the plurality of human body motions.

6. The system of claim 1, wherein, the first health parameter data is collected with a visible light camera positioned to receive light emitted from the transparent material.

7. The system of claim 1, wherein, the one or more sensors includes a plurality of acoustic sensors and a plurality of electrical sensors.

8. The system of claim 7, wherein, the one or more wearable devices includes a plurality of acoustic actuators and a plurality of electrical actuators.

9. The system of claim 1, wherein, the first health parameter data represents a pressure map formed by feet of a subject positioned on the first measurement surface.

10. A health parameter monitoring system comprising:

a first measurement surface defined by transparent material forming a platform with one or more light surfaces positioned to provide light into the transparent material and cause a Frustrated Total Internal Reflection (FTIR) event responsive to contact at the first measurement surface;

a camera positioned to detect light from the FTIR event;

one or more force sensors disposed below the first measurement surface operable to generate force value data responsive to a force applied to the first measurement surface;

one or more second measurement surfaces defined by one or more inner surfaces of one or more wearable devices, the one or more wearable devices include one or more sensors operable to collect data at the one or more second measurement surfaces; and a computing device including one or more non-transitory storage media storing instructions that, when executed by one or more processors, cause the computing device to:

collect first health parameter data from the first measurement surface based on the light detected by the camera;

collect second health parameter data from the one or more second measurement surfaces using the one or more sensors; and normalize the first health parameter data based on the force value data.

11. The system of claim 10, wherein, the one or more sensors include a plurality of acoustic actuators and a plurality of acoustic sensor.

12. The system of claim 11, wherein, the one or more sensors include a plurality of electrical actuators and a plurality of electrical sensors.

13. The system of claim 10, wherein, the one or more wearable devices include a plurality of wearable sleeve devices; and the one or more second measurement surfaces include a plurality of second measurement surfaces formed by the plurality of wearable sleeve devices.

14. A method of monitoring health parameters, the method comprising:

collecting first health parameter data at a first measurement surface defined by transparent material forming a platform with one or more light surfaces positioned to provide light into the transparent material and cause a Frustrated Total Internal Reflection (FTIR) event responsive to contact at the first measurement surface;

collecting second health parameter data at one or more second measurement surfaces defined by one or more inner surfaces of one or more wearable devices, the second measurement surface contacts a target area on an arm, a leg, or a torso of a subject, the one or more wearable devices include one or more sensors operable to detect at least an acoustic signal, based on an acoustic stimulus provided to the arm, the leg, or the torso, at the one or more second measurement surfaces;

determining a locomotion-related characteristic of a subject based on the first health parameter data and the second health parameter data; and causing an indication of the locomotion-related characteristic to be presented at a display of a computing device.

15. The method of claim 14, wherein, collecting the first health parameter data includes receiving, at a camera disposed below the platform, light scattered from the FTIR event.

16. The method of claim 14, further comprising:

presenting, at a virtual reality (VR) headset display, locomotion regimen information including instruction for one or more human body motions; and detecting the one or more human body motions based on the first health parameter data and the second health parameter data.

17. The method of claim 16, wherein, determining the locomotion-related characteristic includes:

determining a pressure distribution based on the first health parameter data; and determining a muscle activation or a nerve activation based on the second health parameter data.

18. The method of claim 14, wherein the acoustic signal represents tissue activity data corresponding at least in part to the acoustic stimulus.

19. The method of claim 14, wherein the one or more wearable devices includes an acoustic actuator for providing the acoustic stimulus and an acoustic sensor for detecting the acoustic signal.

20. The method of claim 19, wherein the one or more sensors includes an electrical sensor for detecting an electrical signal responsive to the acoustic stimulus.

* * * * *